United States Patent [19]
Carol

[11] Patent Number: 4,955,891
[45] Date of Patent: Sep. 11, 1990

[54] METHOD AND APPARATUS FOR PERFORMING STEREOTACTIC SURGERY

[75] Inventor: Mark P. Carol, Tampa, Fla.

[73] Assignee: Ohio Medical Instrument Company, Inc., Cincinnati, Ohio

[21] Appl. No.: 111,987

[22] Filed: Oct. 22, 1987

Related U.S. Application Data

[63] Continuation-in-part of Ser. No. 751,213, Jul. 2, 1985, Pat. No. 4,805,815.

[51] Int. Cl.⁵ ............................................. A61B 19/00
[52] U.S. Cl. .................................... 606/130; 403/91
[58] Field of Search .................. 128/303 B, 395, 630; 33/515, 511; 604/116; 269/328; 403/90, 131, 115; 606/129, 130

[56] References Cited

U.S. PATENT DOCUMENTS

| | | | |
|---|---|---|---|
| 1,516,795 | 11/1924 | Schwarting | 269/328 |
| 2,697,433 | 12/1954 | Zehnder | 128/303 B |
| 3,457,922 | 7/1969 | Ray | 128/303 B |
| 4,638,798 | 1/1987 | Sheldon et al. | 128/303 B |

OTHER PUBLICATIONS

"Wells Stereotaxic Guides"; Rand-Wells Pallidothalamectomy Guide; 1 page; Undated.

*Primary Examiner*—John D. Yasko
*Assistant Examiner*—William Lewis
*Attorney, Agent, or Firm*—Ben D. Tobor

[57] ABSTRACT

A method and apparatus for performing stereotactic surgery upon a target within a skull establishes a first, predetermined geometric relationship between a positioning fixture mounted on the skull and a scanning table surface upon which the skull is supported; and that geometric relationship is duplicated in a phantom fixture. An arc device permits entry into the skull by a medical instrument from a plurality of locations upon the skull.

28 Claims, 10 Drawing Sheets

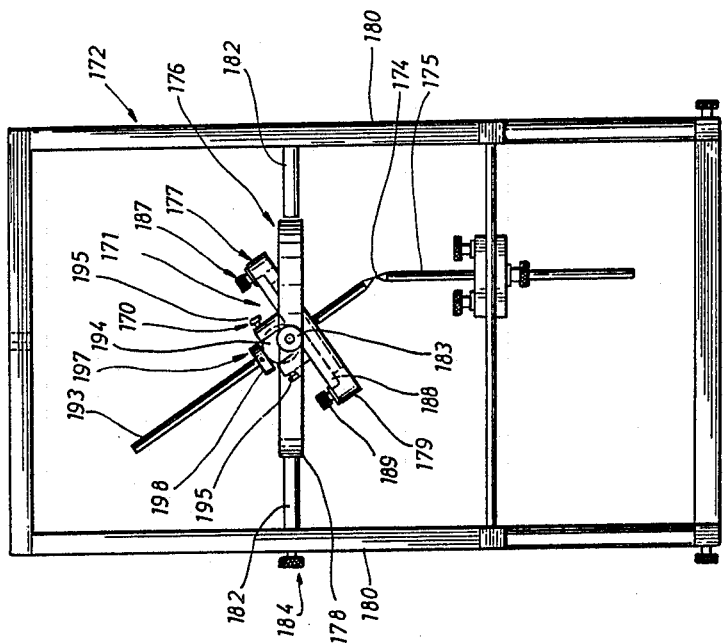
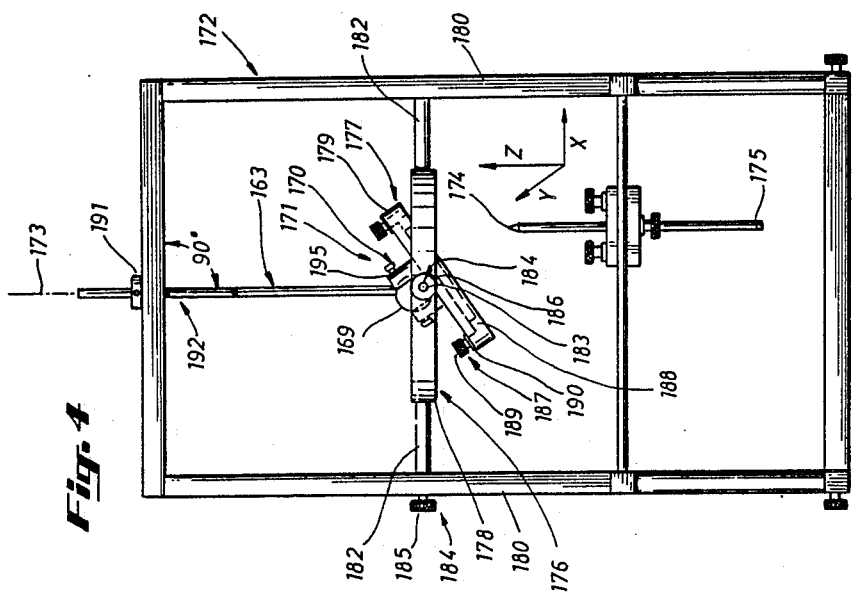

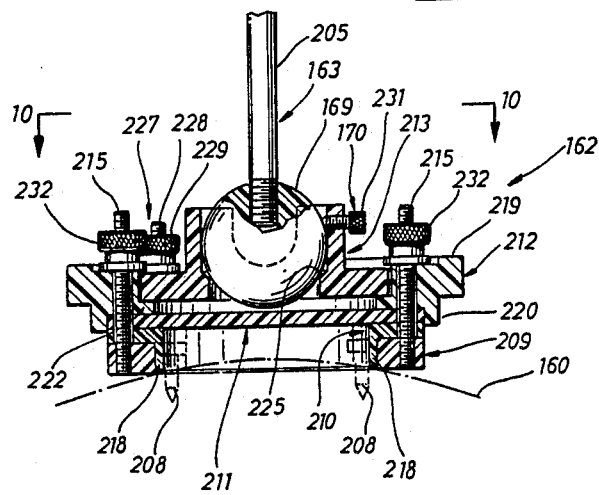
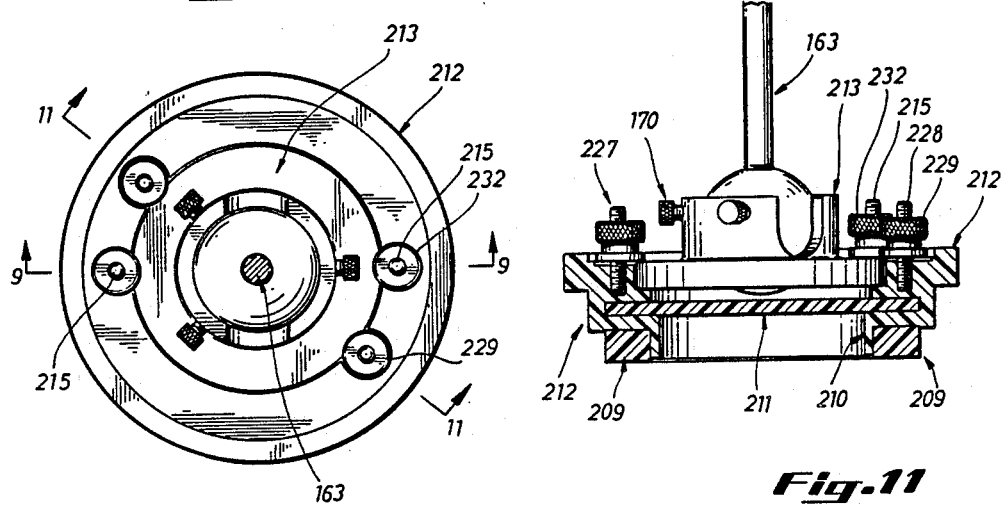

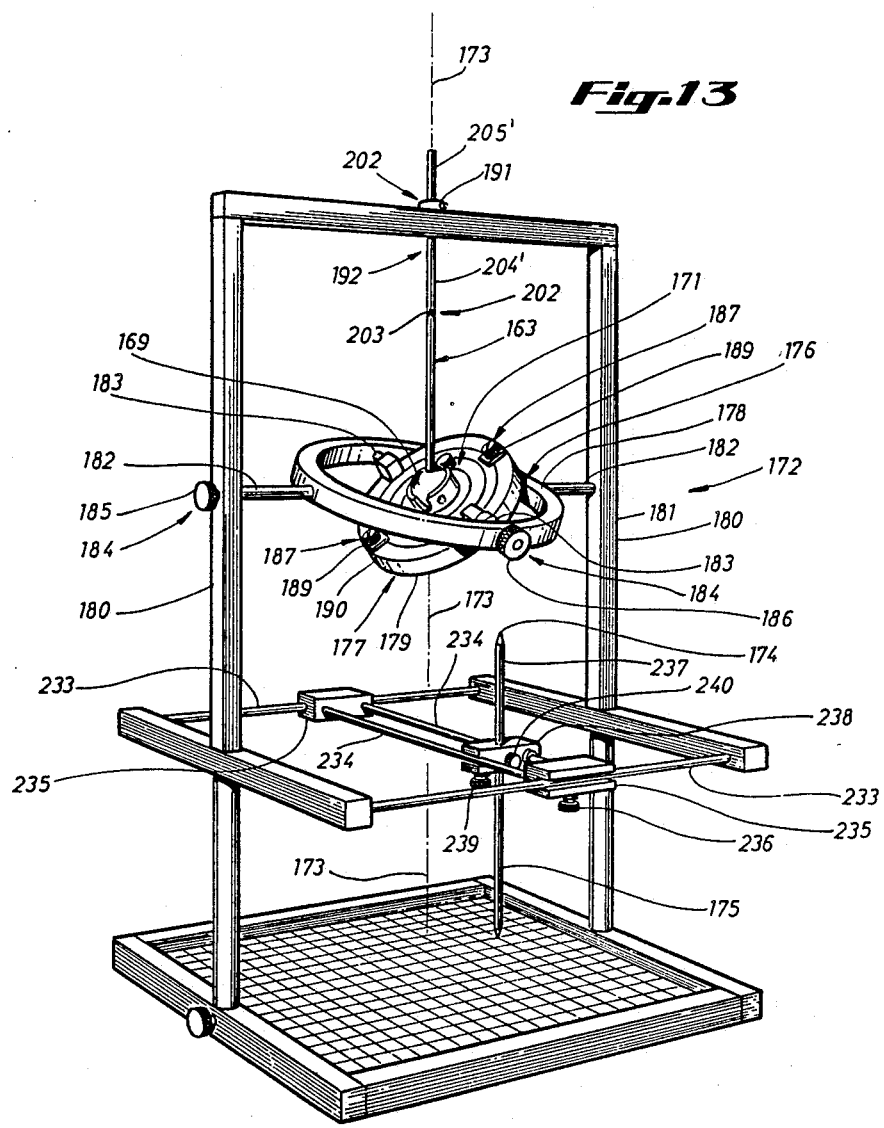

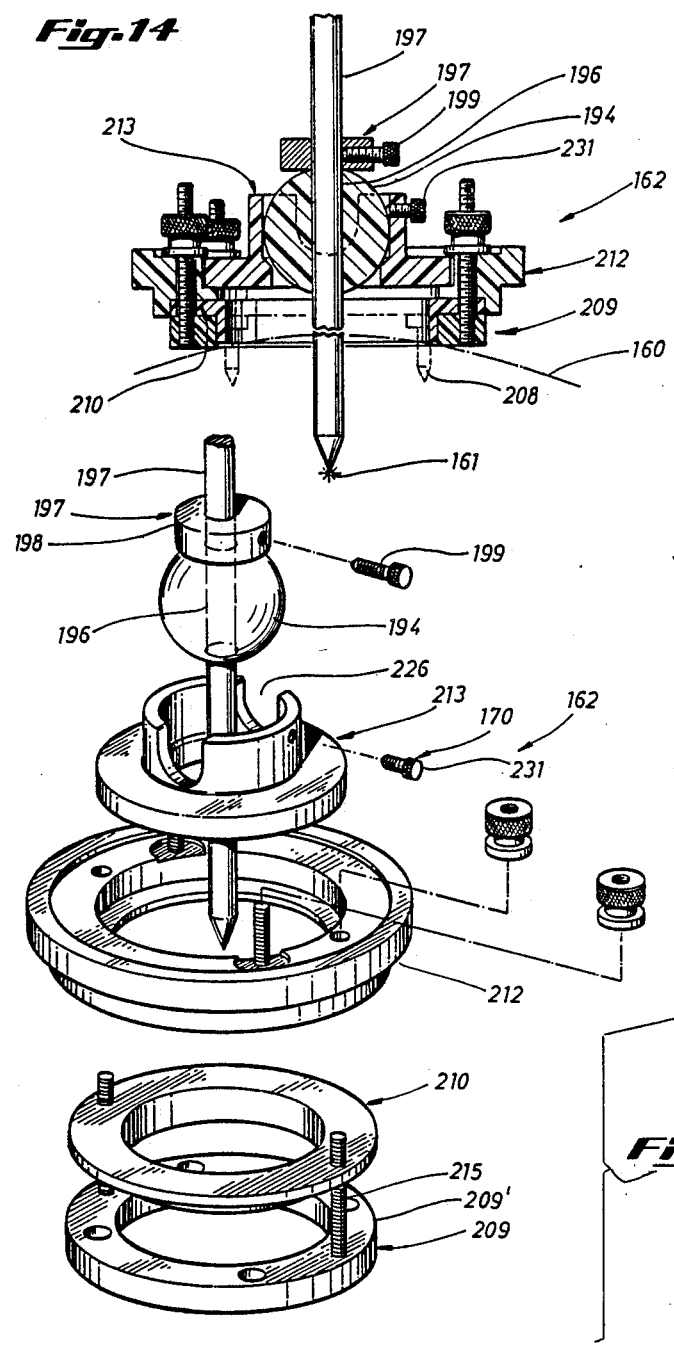

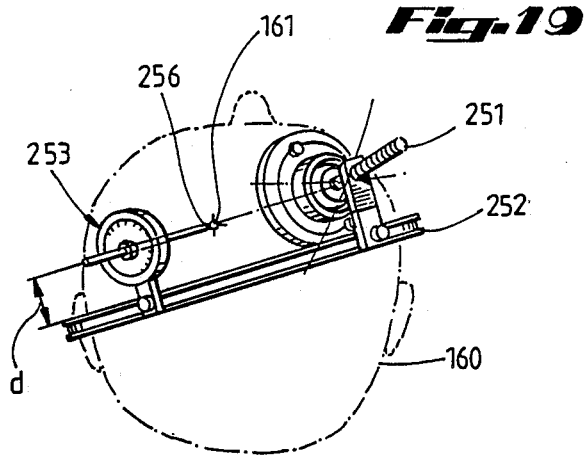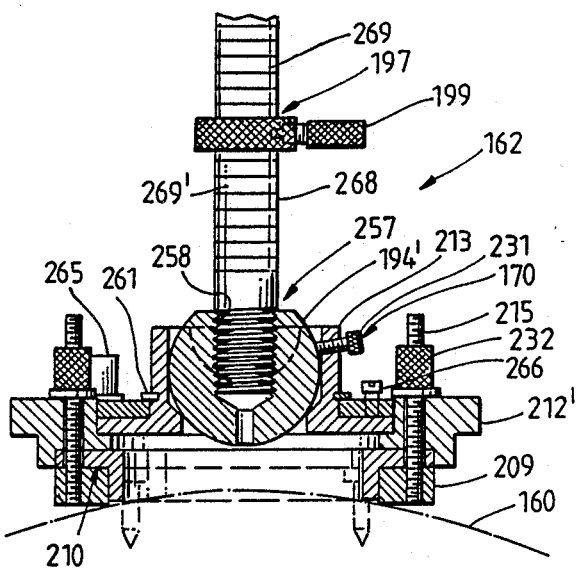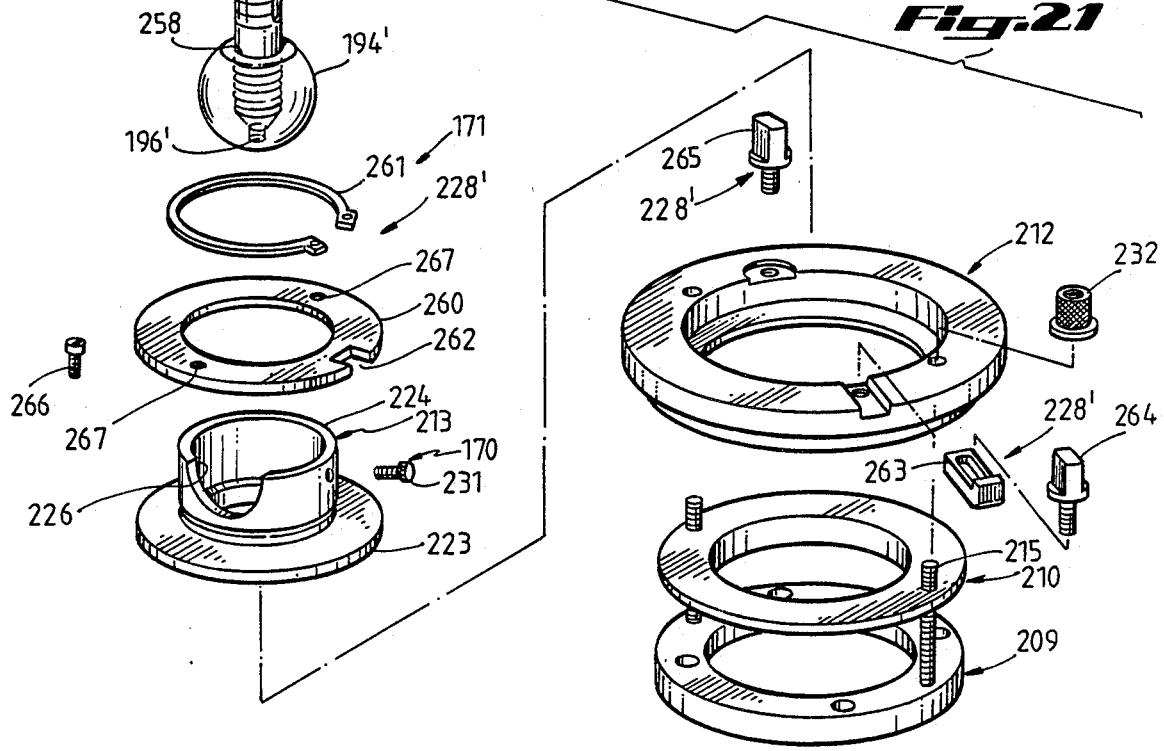

METHOD AND APPARATUS FOR PERFORMING STEREOTACTIC SURGERY

RELATED APPLICATIONS

This application is a continuation-in-part application of applicant's co-pending application, application serial No. 06/751,213, filed July 2, 1985, now U.S. Pat. No. 4,805,815 and entitled Method and Apparatus For Performing Stereotactic Surgery.

FIELD OF THE INVENTION

The invention relates to a method and apparatus for performing stereotactic surgery with a medical instrument upon a target within a skull.

DESCRIPTION OF THE PRIOR ART

One of the ongoing interests of neurosurgeons is the practice of stereotactic surgery: gaining precise access to a specific point in the cranium through the application of an external three-dimensional coordinate system. Much time and effort has gone into the development of instrumentation for implementing such an approach to the human brain. With the development of computerized tomographic ("CT") scanning, and its precise imaging, stereotactic surgery is becoming the diagnostic and therapeutic procedure of choice for many disorders involving the intracranial cavity.

CT scanning produces an image representing a "slice" of brain tissue displayed with anatomical accuracy. The series of "slices", which constitute the complete CT study, represent a three-dimensional picture of the brain, defining the relationship of neurological structures or accurately localizing lesions. CT scanning has allowed physicians to visualize the brain directly, thus making identification of anatomical and pathological areas of interest much more precise, and thus much more accessible to the precise mechanics of stereotactic surgery. Mating CT scanning and stereotactic surgery involves a coordinate transformation from the two-dimensional space of CT scanning to the three-dimensional space of stereotactic surgery.

Although there has been a wide range of methods and devices designed to implement such a coordinate conversion, most of the devices have had a similar conceptual approach, wherein the resulting devices have left stereotactic surgery as being perceived as an esoteric, cumbersome, expensive, and time consuming procedure.

These prior art devices and methods typically utilize a frame mounted to the patient's skull by four pins or screws. Such devices have been found to be quite accurate and reliable and have allowed targets within a skull to be accessed with an accuracy of 1 mm. or less. They have allowed small, relatively inaccessible tumors to be biopsied with minor morbidity and practically absent mortality. These devices have also given surgeons a means of biopsying accessible tumors that are radiosensitive without the need for a formal craniotomy, a procedure that carries a much higher mortality and morbidity than stereotactic surgical procedures. In addition, such devices have provided a means for implementing new modalities for treating hematomas and abscesses, as well as the placement of radioisotopes and chemotherapeutic agents in the treatment of malignant brain tumors.

Despite these advances, there are characteristics of current stereotactic instruments which have severely limited their potential widespread application. The performance of careful stereotactic procedures on a regular basis with the prior art systems available requires much operating room time to be wasted during the procedure. Processing of X-ray pictures, target point calculations, and cumbersome mechanical adjustments on stereotactic frames add time to the operation. The inability of these systems to be reused on the same patient without recalculating target points also adds to their inefficiency. Although the prior art stereotactic instruments are adequate for reaching a single intracranial target point, rapid access to multiple targets during a procedure is inconvenient. Furthermore, the prior art devices are extremely expensive and are quite complicated to employ, thereby making their appeal to the surgeon in private practice quite limited. Some of the prior art systems require modifications of existing CT scanning software, or alternatively, require software generated coordinates determined from a hand-held calculator as part of the system. The frame required by these prior art devices requires fixation to the skull of the patient, typically via four screws, whereby the frame is quite cumbersome and uncomfortable. Additionally, the frame cannot be left on the patient's head if the same procedure is to be repeated at a later date. If subsequent stereotactic procedures are to be performed, the frame must be reapplied at the time of the second procedure, including the step of again using a CT scanner to calculate the coordinates of the target point within the skull.

Accordingly, prior to the development of the present method and apparatus for performing stereotactic surgery, there has been no method and apparatus for performing stereotactic surgery which: is compact, inexpensive, easy to use, precise, and comfortable; permits reaccessing of a target within the skull without additional CT scanning and coordinate recalculation; and does not require a bulky skull mounted frame. Therefore, the art has sought a method and an apparatus for performing stereotactic surgery which: does not require a skull mounted frame; is compact, inexpensive, easy to use, precise and comfortable; and permits reaccessing a target within the skull without re-scanning and coordinate recalculation.

SUMMARY OF THE INVENTION

In accordance with the invention, the foregoing advantages have been achieved through the present method and apparatus for performing stereotactic surgery. The method for performing stereotactic surgery, in accordance with the present invention, includes the steps of: establishing a first, pre-determined geometric relationship between a positioning fixture attached to both the skull and to a support surface upon which the skull is disposed; scanning the skull to produce an image of the target within the skull with respect to the positioning fixture; transferring at least a portion of the positioning fixture to a phantom fixture and disposing the positioning fixture portion with respect to the phantom fixture to establish a second, predetermined geometric relationship therebetween, which is identical to the first, predetermined geometric relationship, whereby the slope of the skull where the positioning fixture is attached to the skull is duplicated within the phantom fixture; disposing a phantom target within the phantom fixture at a location which corresponds to the location of the target within the skull; determining the trajectory and distance of a medical instrument extending from the positioning fixture portion to the phantom target; attaching the portion of the positioning fixture to the skull in the same location it was originally attached to the skull; attaching a carrier member, arc member, and instrument guide member to the positioning fixture; and inserting the medical instrument through the instrument guide member whereby the medical instrument will intersect the target in the skull.

Another feature of the present invention is that the positioning fixture may be attached to the support surface by an attachment member having first and second end portions and the first predetermined geometric relationship is the attachment member disposed coplanar with the support surface; and the second, predetermined geometric relationship is the attachment member disposed coplanar with the phantom fixture. A further feature of the present invention includes the steps of: moveably associating the first end portion of the attachment member with respect to the positioning fixture; and securing the attachment member with respect to the positioning fixture prior to scanning the skull.

A further feature of the present invention may include the steps of: moveably associating the attachment member with respect to at least a portion of the positioning fixture by using a first positioning ball secured to the first end portion of the attachment member; and the first positioning ball may be rotatably received within the positioning fixture.

Another feature of the present invention may include the steps of: using an outer and inner gimbal in the phantom fixture; and disposing the positioning fixture portion within the inner gimbal in the second, predetermined geometric relationship. A further feature of the present invention is that the positioning fixture may be attached to the support surface by an attachment member having first and second end portions; the first, predetermined geometric relationship is the attachment member disposed coplanar with the support surface; the second geometric relationship is the attachment member orthogonally disposed with respect to the phantom fixture; and while the positioning fixture portion is fixed with respect to the attachment member, the outer and inner gimbals are adjusted to receive the positioning fixture portion.

Another feature of the present invention may include the step of locating the instrument guide member upon the arc member, whereby the medical instrument may enter the skull at a desired location upon the skull. A further feature may include the step of rotating the arc member about the carrier member whereby the medical instrument may enter the skull at a desired location upon the skull.

In accordance with the invention, the foregoing advantages have been achieved through the present system for performing stereotactic surgery. The system for performing stereotactic surgery, in accordance with the present invention, may include: a positioning fixture having associated therewith, a means for attaching the positioning fixture to both the skull and to a support surface upon which the skull is disposed; the positioning fixture including means for establishing a first, predetermined geometric relationship between the positioning fixture and the support surface; and a phantom fixture, which may include: means for receiving at least a portion of the positioning fixture; means for establishing a second, predetermined geometric relationship between the positioning fixture portion and the phantom fixture, wherein the second geometric relationship is identical to the first geometric relationship, whereby the slope of the skull where the positioning fixture is attached to the skull may be duplicated within the phantom fixture; and a carrier member adapted for attachment to the positioning fixture, an arc member, adapted for attachment to the carrier member, and an instrument guide member, adapted to be attached to the arc member, whereby the medical instrument may be passed through the instrument guide member to intersect the target by entering the skull at a plurality of locations upon the skull.

Another feature of the system in accordance with the present invention is that the means for attaching the positioning fixture may include an attachment member having first and second end portions; in the first, predetermined geometric relationship, the attachment member is disposed coplanar with the support surface; and in the second, predetermined geometric relationship, the attachment member is disposed coplanar with the phantom fixture.

An additional feature of the system of the present invention is that the means for establishing the first, predetermined geometric relationship, may include the first end portion of the attachment member being moveably associated with respect to the positioning fixture; and the positioning fixture may include means for locking the attachment member with respect to at least a portion of the positioning fixture. A further feature of the system of the present invention is that the first end portion of the attachment member may have a positioning ball associated therewith; and a portion of the positioning fixture may include means for rotatably receiving the positioning ball therein. The rotatable receiving means may comprise a ball socket member. A further feature of the system of the present invention is that the ball socket member may have an arc-trajectory ball disposed therein, upon the removal of the positioning ball. The arc-trajectory ball may have a passageway therethrough adapted to permit a medical instrument to pass through the arc-trajectory ball, and the arc-trajectory ball may include means for attaching the carrier member to the positioning fixture. An additional feature of the system of the present invention is that the instrument guide member may include means for include means for guiding the medical instrument to predetermined locations within the skull, which locations are offset from the target in the skull.

In accordance with the invention, the foregoing advantages have been achieved through present apparatus, useful for performing stereotactic surgery. The apparatus, useful for performing stereotactic surgery, may include: a skull plate member, adapted to be secured to a skull; a secondary plate member adapted to overlie the skull plate member; a ball socket member rotatably received within the secondary plate member; means for aligning the skull plate member and secondary plate member with respect to one another; means for locking the ball socket member with respect to the secondary plate member; an arc-trajectory ball disposed within the ball socket member; a carrier member attached to the arc-trajectory ball; an arc member mounted on the carrier member; and an instrument guide member mounted on the arc member. An additional feature of the apparatus of the present invention is that the apparatus may include means for locking the arc-trajectory ball within the ball socket member. A further feature of the apparatus of the present invention is that the arc member may be adjustably mounted on the carrier member. The instrument guide member may also be adjustably mounted on the arc member. Another feature of the present invention is that the instrument guide member may include an opening for guiding a medical instrument and means for moving the opening with respect to the instrument guide member.

The method and apparatus for performing stereotactic surgery of the present invention, when compared with previously proposed prior art methods and apparatus, have the advantages of being: compact, inexpensive, easy to use, precise, and comfortable for the patient; does not require a skull mounted frame; and permits reaccessing target areas within the skull without recalculating coordinates or rescanning the skull.

BRIEF DESCRIPTION OF THE DRAWINGS

In the drawings:

FIG. 1 is a front view of a patient (shown in dotted lines) with the positioning fixture of the present invention disposed upon the patient's skull;

FIG. 2 is a top view of a patient (shown in dotted lines) being disposed upon a support surface, with the positioning fixture of the present invention disposed on the patient's skull;

FIG. 3 is a side view of a patient (shown in dotted lines) disposed upon a support surface with the positioning fixture of the present invention disposed on the patient's skull;

FIG. 4 is a front view of a phantom fixture in accordance with the present invention;

FIG. 5 is another front view of a phantom fixture in accordance with the present invention;

FIG. 9 is a partial cross-sectional view of the positioning fixture taken along line 9—9 of FIG. 10;

FIG. 10 is a partial cross-sectional view of the positioning fixture taken along line 10—10 of FIG. 9;

FIG. 11 is a partial cross-sectional view of the positioning fixture of the present invention taken along line 11—11 of FIG. 10;

FIG. 13 is a perspective view of a phantom fixture of the present invention;

FIG. 14 is a partial cross-sectional view of a positioning fixture of the present invention, including a medical instrument disposed therein;

FIG. 15 is a perspective, exploded view of the positioning fixture of FIG. 14;

FIG. 19 is a top view of a patient having an apparatus, useful for performing stereotactic surgery, in accordance with the present invention upon the patient's skull;

FIG. 20 is a partial cross-sectional view of an apparatus in accordance with the present invention, useful for performing stereotactic surgery;

FIG. 21 is a an exploded view of the apparatus of FIG. 20;

Figure 8:
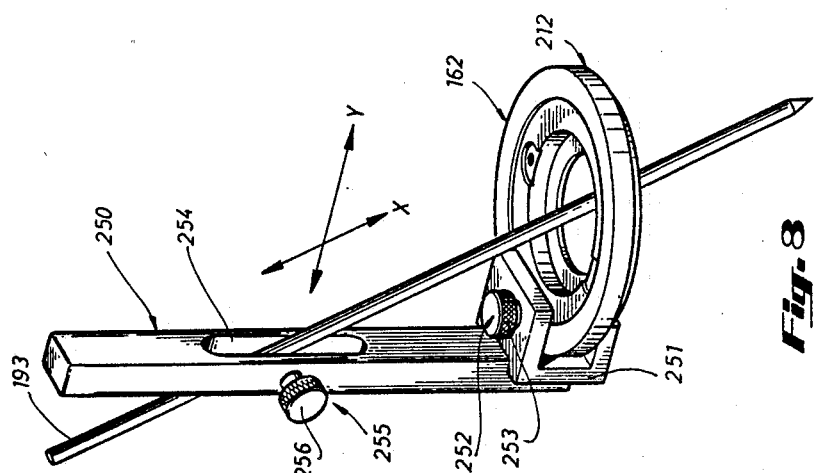
FIG. 8 is a perspective view of a stanchion clamp accessory for use with the present invention.

While the invention will be described in connection with the preferred embodiment, it will be understood that it is not intended to limit the invention to that embodiment. On the contrary, it is intended to cover all alternatives, modifications, and equivalents as may be included within the spirit and scope of the invention as defined by the appended claims.

DETAILED DESCRIPTION OF THE INVENTION

Figures 1, 2, 3:
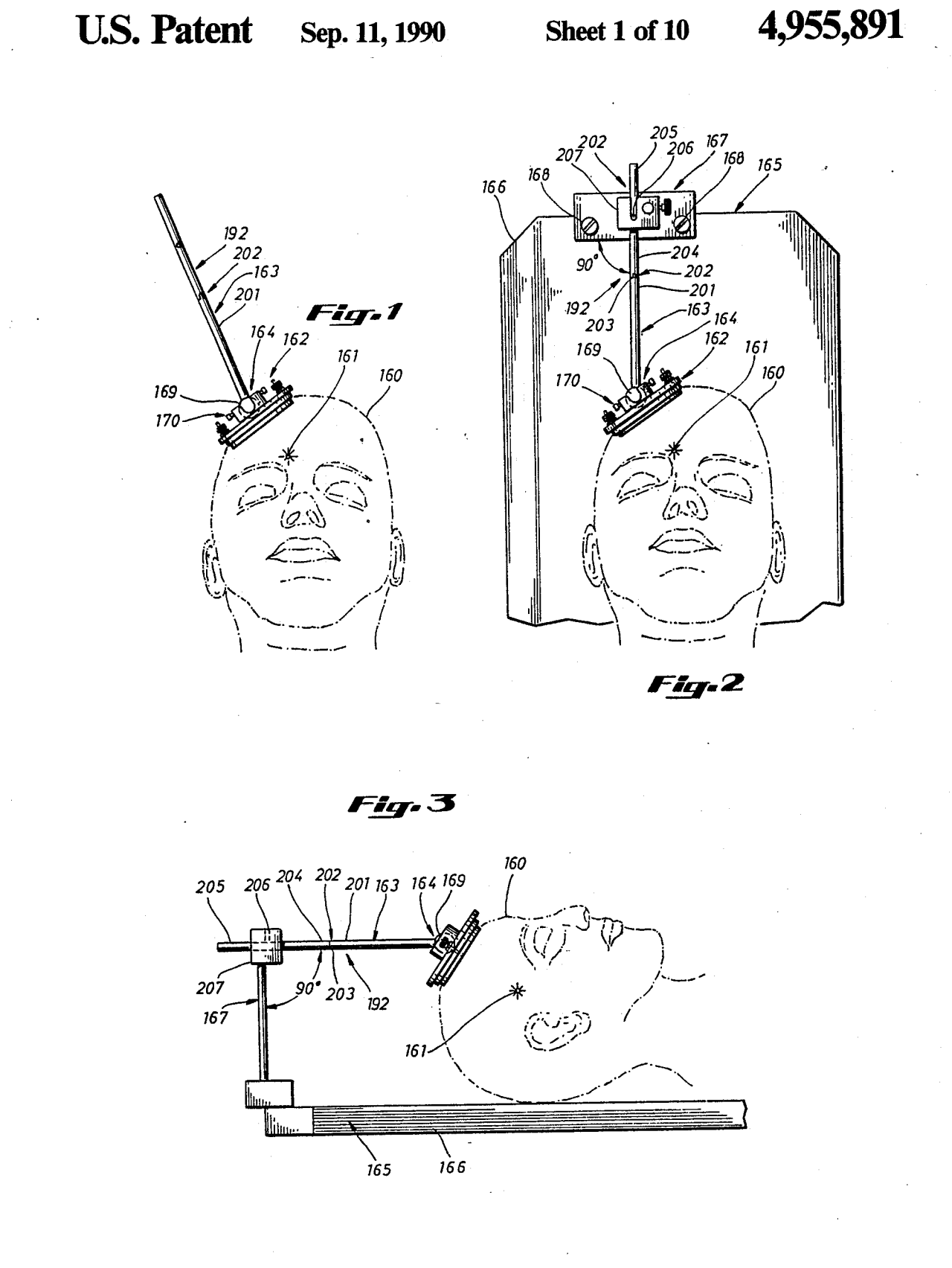

With respect to FIGS. 1–6, the method for performing stereotactic surgery with a medical instrument upon a target within a skull will be generally described. Throughout FIGS. 1–6, the patient's skull 160 is shown in dotted lines, and target 161 is illustrated to represent the abnormality which is desired to be treated. For example, target 161 could be a hematoma, abscess or tumor. With reference to FIG. 1, a positioning fixture 162 is attached to skull 160 in a manner to be hereinafter described in greater detail. Preferably, positioning fixture 162 is constructed in accordance with the present invention, as will be hereinafter described in greater detail. The location at which positioning fixture 162 is attached to skull 160 may be determined by the location of target 161 within skull 160, as well as by a trial fit of positioning fixture 162 to skull 160. As seen in FIGS. 1–3, positioning fixture 162 may have an attachment member 163 associated therewith. Attachment member 163 has a first end portion 164 moveably associated with respect to positioning fixture 162, as will be hereinafter described in greater detail.

With reference to FIGS. 2 and 3, the patient is laid upon a support surface 165 and skull 160 is thus disposed upon support surface 165. Typically, support surface 165 is a conventional, planar imaging table 166 which is used in connection with a conventional scanning device, such as a CT scanner. As seen in FIGS. 2 and 3, attachment member 163 is moved with respect to positioning fixture 162, so that attachment member 163 may mate with an upright bracket 167 which is secured to imaging table 166 in any suitable fashion, such as by a clamp or screws 168. With the positioning fixture 162 and attachment member 163 in the positions illustrated in FIGS. 2 and 3, a first, predetermined geometric relationship has been established between the positioning fixture 162 and the support surface 165 upon which skull 160 is disposed. Preferably, this first, pre-determined geometric relationship is with attachment member 163 being disposed coplanar with support surface 165. By use of the term "coplanar" it is meant that the longitudinal axis of attachment member 163 is caused to lie in a plane which is parallel with the longitudinal axis of the support surface 165, as seen in FIG. 3, and in a plane which is perpendicular to the support surface 165, as seen in FIG. 2.

With the patient's skull 160 disposed upon support surface 165, as shown in FIGS. 2 and 3, and the attachment member disposed in the first, predetermined geometric relationship with respect to support surface 165 and attached therebetween, the skull is then scanned by any suitable scanning device, such as a CT scanner, in a conventional manner. A radiopaque marker (not shown) is disposed in the center of the positioning fixture 162, whereby the scanning procedure produces a series of images of the target 161 with respect to the positioning fixture 162. After the scanning of skull 160 has been performed, at least a portion 171 of the positioning fixture 162 may be removed from the patient's skull 160 and transferred to a phantom fixture 172, as shown in FIG. 4. In this regard, preferably only a portion 171 of positioning fixture 162 is removed from skull 160; however, it is possible that the entire positioning fixture 162 could be removed from the patient's skull 160. Further, it should be noted that in contrast to the prior art methods and devices previously described, if a portion of positioning fixture 162 remains on skull 160, such positioning fixture portion is much more compact with respect to the patient's skull 160, as well as being much more comfortable for the patient.

Further, with regard to FIGS. 1-3, it is seen that the first end portion 164 of attachment member 163 may be moveably associated with respect to positioning fixture 162, as by securing the first end portion 164 of attachment member 163 to a positioning ball 169, and positioning ball 169 is rotatably received within the positioning fixture 162. Accordingly, attachment member 163 may be freely moved with respect to positioning fixture 162, whereby attachment member 163 can be disposed in the geometric relationship shown in FIGS. 2 and 3. Positioning fixture 162 may also be provided with a means for securing, or locking, 170 the attachment member 163 with respect to positioning fixture 162. Prior to scanning the skull 160, when attachment member 163 and positioning fixture 162 are disposed in the geometric relationship shown in FIGS. 2 and 3, positioning ball locking means 170, to be hereinafter described in greater detail, is preferably engaged, whereby skull 160, attachment member 163 and positioning fixture 162 will remain disposed in the geometric relationship shown in FIGS. 2 and 3 throughout the scanning procedure. After the scanning procedure has been performed, the portion 171 of positioning fixture 162 is transferred to phantom fixture 172. Preferably, positioning fixture portion 171 includes attachment member 163, positioning ball 169, and positioning ball locking means 170, as shown in FIG. 4, and as will be hereinafter described in greater detail.

With reference to FIG. 4, the positioning fixture portion 171, including attachment member 163 and positioning ball 169, which remains in the locked position shown in FIGS. 2 and 3, has been transferred to phantom fixture 172, and is disposed with respect to phantom fixture 172 in a second, predetermined geometric relationship therebetween. The second, predetermined geometric relationship is shown as being attachment member 163 being disposed coplanar with phantom fixture 172. In this regard, the term "coplanar" is defined as meaning that the attachment member 163 lies in planes which are all parallel with respect to the longitudinal axis 173 (as shown in dotted lines in FIGS. 4 and 13), of the phantom fixture 172. Thus, the second, predetermined geometric relationship between positioning fixture portion 171 and phantom fixture 172 is identical to the first, predetermined geometric relationship between positioning fixture 162 and support surface 165. Since the positioning fixture portion 171 disposed within phantom fixture 172 was originally disposed upon skull 160, the slope of skull 160 at the location where positioning fixture 162 was attached to skull 160 has been duplicated within phantom fixture 172. In summary, with the attachment member 163, including positioning fixture portion 171 secured thereto, disposed within phantom fixture 172 in the same position as shown in FIGS. 2 and 3, the second geometric relationship between the attachment member 163 and the phantom fixture 172 is the same as the first geometric relationship between the attachment member and support surface 165. Since the disposition of attachment member 163 with respect to the positioning fixture portion 171 is identical in FIGS. 2 and 3, and FIG. 4, and since positioning ball 169 has been locked with respect to positioning fixture 162, the slope of the skull 160 where the positioning fixture 162 has been attached to skull 160 is duplicated within the phantom fixture 172.

Still with reference to FIG. 4, a phantom target 174 is disposed within the phantom fixture 172 at a location which corresponds to the location of the target 161 within skull 160. The three-dimensional spatial coordinates of phantom target 174, representative of target 161 within skull 160, are determined in a conventional manner from the scanning procedure. The x and y coordinates of the target 161 within skull 160 may be read from the generated images from the scanning procedure and the z coordinate may be obtained by noting the difference in imaging table 166 displacement between the image slice containing the positioning fixture 162 and the image slice containing the target 161, insofar as the series of generated images disclose the target with respect to positioning fixture 162. In this regard, a radiopaque marker (not shown) is preferably disposed at the center of positioning ball 169, and, as will hereinafter be described in greater detail, the positioning fixture 162, including positioning ball 169 are made of a radiolucent material, such as LEXAN ®, so as not to interfere with the images produced by the scanning procedure. Thus, the coordinates of the target 161 are generated in relation to the positioning fixture 162. They can then be transferred to the phantom fixture 172 in a conventional manner, so that phantom target 174, which is preferably the tip of a phantom target rod 175, may be disposed within phantom fixture 172 at a spatial location which corresponds to the location of the target 161 within skull 160. Target rod 175, and in turn phantom target 174, may be disposed anywhere within phantom fixture 172 in a conventional manner, as will hereinafter be described in greater detail in connection with FIG. 13.

With reference to FIGS. 4 and 13, phantom fixture 172 preferably utilizes an outer and inner gimbal 176, 177. As seen in FIGS. 4 and 13, the positioning fixture portion 171 is disposed within the inner gimbal 177. Preferably, outer and inner gimbals 176, 177 are constructed as an outer gimbal ring 178 and an inner gimbal ring 179. Outer gimbal 176 may be preferably disposed between two upright frame members 180 which form a portion of a frame 181 of phantom fixture 172. Outer gimbal 176 may be rotated about an axis defined by two rod members 182 journaled within uprights 180. Likewise, inner gimbal 177 is mounted within outer gimbal 176 as to be freely rotatable with respect to outer gimbal 176, as by mounting inner gimbal 177 upon rod members 183 which are rotatably mounted in outer gimbal 176. Outer and inner gimbals 176, 177 may be rotated independently, the inner gimbal 177 rotating within outer gimbal 176. Thus, by adjusting the rotation of the outer and inner gimbals 176, 177 within phantom fixture 172, the inner gimbal 177 can be adjusted to receive the positioning fixture portion 171 when positioning fixture portion 171 is transferred, along with attachment member 163 in its locked position with respect to positioning fixture 171, and thus disposed within phantom fixture 172. Therefore, positioning fixture portion 171 will lie within inner gimbal 177 of phantom fixture 172, so as to be disposed in the second, predetermined geometric relationship previously described. It should of course be understood that the configuration of inner and outer gimbals 177, 176 could be any other configuration other than inner and outer gimbal rings 179, 178, so long as inner gimbal 177 is free to rotate within outer gimbal 176, and outer gimbal 176 can freely rotate within phantom fixture 172. For example, inner gimbal and outer gimbal 177, 176 could have a square configuration, wherein the inner square (not shown) is sized so as to be able to rotate within the outer square (not shown).

Still with reference to FIGS. 4 and 13, phantom fixture 172 may preferably include means for locking 184 the inner and outer gimbals 177, 176 with respect to phantom fixture 172. Preferably, locking means 184 for gimbals 176, 177 may be any suitable device which can lock rod member 182 with respect to uprights 180 of phantom fixture 172, and lock rod members 183 with respect to outer gimbal 176. For example, locking means 184 can comprise two thumb nuts 185, 186. Thumb nut 185 can engage upright 180, thus securing rod member 182, and in turn outer gimbal 176 in a fixed position. Thumb nut 186 can engage outer gimbal 176 which in turn locks the position of rod member 183 with respect to outer gimbal 178. Further, the inner gimbal 177 includes a means for locking 187 the positioning fixture portion 171 with respect to inner gimbal 177. In this regard, as seen in FIG. 4, inner gimbal 177 may be provided with an interior recessed flange member 188 upon which positioning fixture portion 171 rests upon when it is received within inner gimbal 177. Locking means 187, which preferably comprises at least one lock nut 189, and preferably two lock nuts 189, can be threaded downwardly to bear upon a small plate 190 which in turn bears against inner gimbal 177 and positioning fixture portion 171 as shown in FIG. 4. After positioning fixture portion 171, including attachment member 163, are disposed within phantom fixture 172, inner and outer gimbals, 177, 176 are adjusted as previously described. Locking means 184, 187 may then be engaged to lock inner and outer gimbals 177, 176 in the position shown in FIG. 4, and positioning fixture portion 171 is then secured within inner gimbal 177.

After the positioning fixture portion 171 and phantom target 174 have been disposed within phantom fixture 172 as previously described and as illustrated in FIG. 4, it is necessary to determine the trajectory and distance of a medical instrument extending from the positioning fixture portion 171 to the phantom target 174. This is accomplished by releasing positioning ball locking means 170, whereby positioning ball 169 and attachment member 163 may be removed from the phantom fixture 172, leaving the positioning fixture portion 171 disposed within inner gimbal 177 in the locked positions previously described. A suitable lock 191 associated with phantom fixture 172 and engageable with the second end portion 192 of attachment member 163 may be disengaged to permit the removal of attachment member 163 and in turn positioning ball 169 from phantom fixture 172.

The trajectory and distance of a medical instrument extending from the positioning fixture portion 171 to the phantom target 174 is then determined by inserting a medical instrument 193 (FIG. 5) through the positioning fixture portion 171 until it intersects the phantom target 174. The medical instrument 193 may then be locked with respect to the positioning fixture portion 171 at the desired trajectory and distance to the phantom target 174. This step may be accomplished by associating a trajectory ball 194 with the positioning fixture portion 171; inserting the medical instrument 193 through the trajectory ball 194 and adjusting it until it intersects the phantom target 174 as shown in FIG. 5. Trajectory ball 194 may then be locked with respect to positioning fixture portion 171 as by engaging positioning ball locking means 170 with trajectory ball 194. For example, positioning ball locking means 170, which can also be used to lock trajectory ball 194, is preferably at least one, or more, locking screws 195 which securely engage trajectory ball 194 and fix its position with respect to positioning fixture portion 171. Trajectory ball 194 is preferably provided with a passageway 196 (FIGS. 14 and 15) extending therethrough which is adapted to permit the medical instrument 193 to pass through the trajectory ball 194. Medical instrument 193 may be a probe useful for obtaining a portion of a tumor for biopsy purposes, as well as a device which can be utilized to drain an abscess in the brain or to aspirate a cyst.

Still with reference to FIG. 5, after trajectory ball 194 has been locked with respect to positioning fixture portion 171, whereby medical instrument 193 has intersected phantom target 174, the distance from the positioning fixture portion 171 to the phantom target 174 is preferably indicated. The indication of this distance can be accomplished by associating the depth stop member 197 with the medical instrument 193 after trajectory ball 194 has been locked with respect to positioning fixture portion 171. Depth stop member 197 may be a ring 198 which is disposed about medical instrument 193 and includes set screw 199 (FIGS. 14 and 15). Upon engagement of set screw 199 into medical instrument 193, ring 198 prevents further inward movement of medical instrument 193 through trajectory ball 194.

Figure 6:
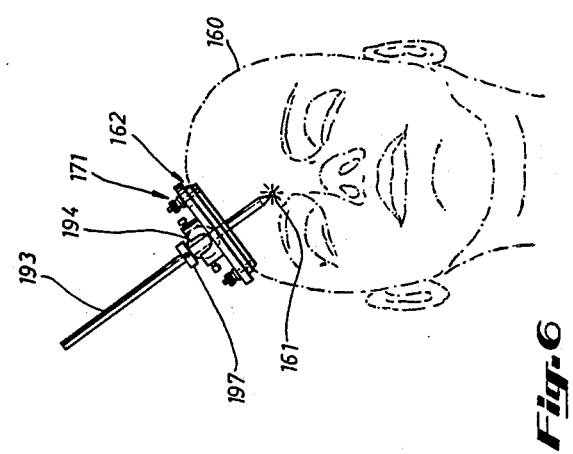
FIG. 6 is a front view of a patient (shown in dotted lines) with the positioning fixture of the present invention being used to direct a medical instrument toward a target within the patient's skull.
Figure 12:
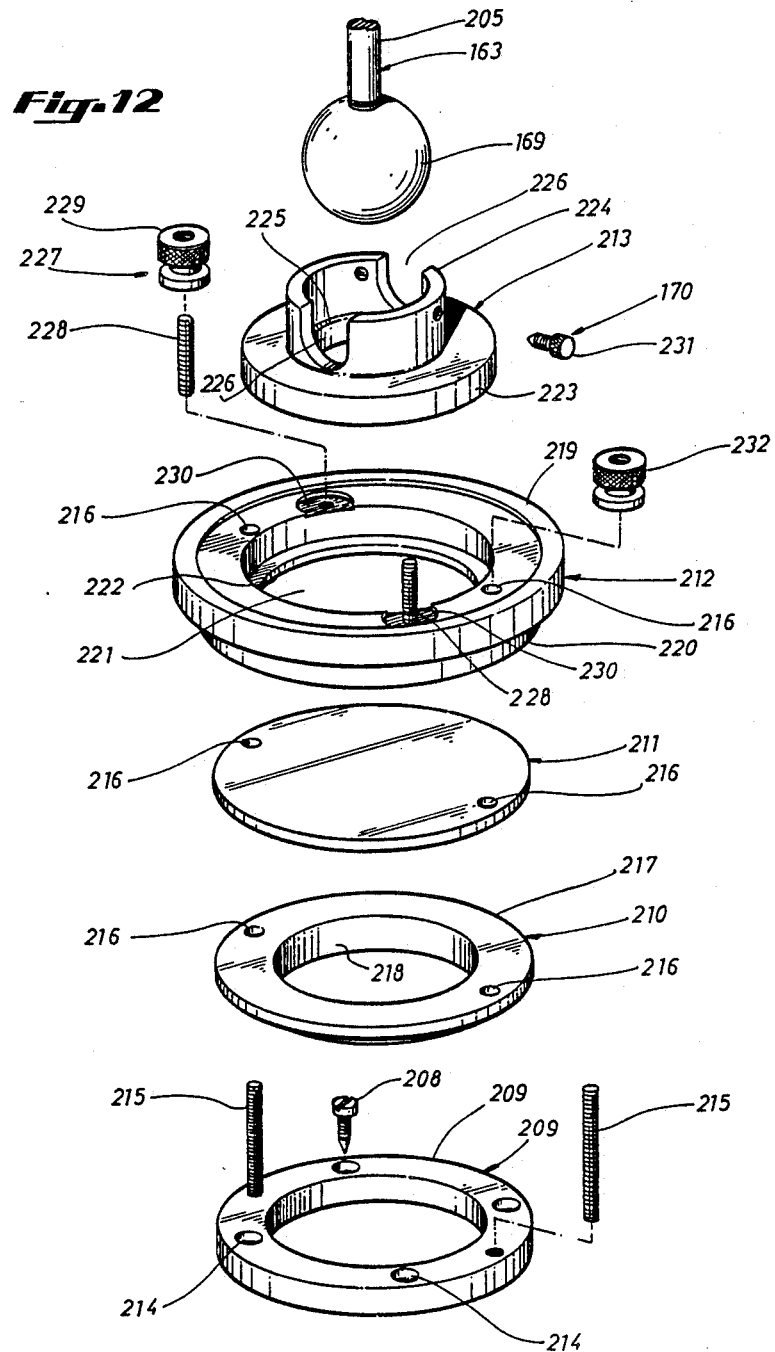
FIG. 12 is a perspective, exploded view of the positioning fixture of the present invention shown in FIGS. 9–11.
Figure 16:
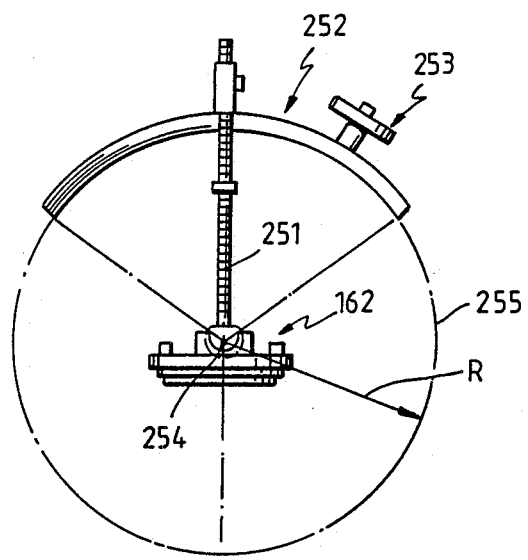
FIGS. 16–18 are plane views illustrating the operation of an apparatus useful for performing stereotactic surgery in accordance with the present invention.

Upon completion of the step of determining the trajectory and distance of the medical instrument 193 to the phantom target 174, locking means 187 is released as by removing lock nuts 189. Positioning fixture portion 171, including medical instrument 193 and the locked trajectory ball 194 may then be removed from the phantom fixture. These components are then sterilized in a conventional manner. After sterilization, the positioning fixture portion 171 is attached upon skull 160, as shown in FIG. 6, in the same location it was originally attached to the skull 160 as shown in FIG. 1. While positioning fixture portion 171 is being reattached to skull 160, trajectory ball 194 remains firmly locked within position fixture portion 171, while medical instrument 193 with depth stop member 197 are kept sterile. It should be noted that prior to or after the attachment of positioning fixture portion 171 to skull 160, skull 160 has had a hole drilled therein in a conventional manner to allow subsequent insertion of medical instrument 193 into skull 160.

Still with reference to FIG. 6, after the positioning fixture portion 171 has been reattached to skull 160 and the requisite hole has been drilled in skull 160, medical instrument 193 is inserted through the positioning fixture 162 in the trajectory determined from the phantom fixture 172, as by trajectory ball 194. The medical instrument 193 is inserted until it intersects the target 161 within skull 160, as shown in FIG. 6. The desired medical treatment of target 161 may then be performed by medical instrument 193.

It should be noted that if instead of only a portion 171 of positioning fixture 162 being utilized within phantom fixture 172, as previously described, the entire positioning fixture 162 could be removed from skull 160 after the first, predetermined geometric relationship was established, as described in connection with FIGS. 2 and 3. The entire positioning fixture 162 would be reattached to skull 160 in the same location it was originally attached to the skull 160 as shown in FIG. 1, prior to insertion of medical instrument 193. It should further be noted that once the trajectory and distance of the medical instrument from the positioning fixture 162 to the target 161 has been determined in the manner previously described, it is possible to store the positioning fixture 162, or positioning fixture portion 171, with the trajectory ball 194 firmly locked in place within positioning fixture 162, along with storing medical instrument 193 with depth stop member 197 firmly engaged therewith. Thus the patient can return at a subsequent date to have the stereotactic surgery performed upon target 161. All that is required is to insure that positioning fixture 162 is reattached to skull 160 at the later time in precisely the same location it was originally attached to the skull 160 as shown in FIG. 1. In this regard, positioning fixture 162, or a portion of a positioning fixture 162, can be secured to skull 160 in a conventional manner by the use of at least one and preferably two or more self-tapping titanium screws. Upon removal of such screws, the positioning fixture 162 can be removed from skull 160 and it can be reattached to the identical site upon skull 160 by utilizing the same positioning fixture 162 at a later date, and securing it to skull 160 with screws engaging the previously formed holes in skull 160. Additionally, a patient's positioning fixture 162 with his trajectory ball 194 firmly locked therein may be stored; and either the medical instrument 193 with depth stop member 197 firmly locked thereon may be stored, or, alternatively, a record of the distance from the depth stop member to either end of the medical instrument 193 may be retained. Thus, a patient can return for subsequent stereotactic surgery treatments on the same target 161, without the necessity of rescanning the patient's skull 160 and performing the steps utilizing the phantom fixture.

In practicing the foregoing described method, it is preferred to utilize an elongate rod 201 (FIGS. 1–3) for attachment member 163, and to include a means for identically orientating 202 the second end portion 192 of attachment member 163 with respect to both the support surface 165 and the phantom fixture 172. With reference to FIGS. 2, 3, and 13, a mating tongue and groove connection can be used as the means for identically orientating 202 the second end portion 192 of the attachment member 163. Preferably the mating tongue and groove connection 203 is associated with the second end 192 of attachment member 163 and an end 204 of an elongate rod 205 disposed coplanar with respect to the support surface 165 (FIGS. 2 and 3) and an end 204' of an elongate rod 205' disposed coplanar with respect to the phantom fixture 172, as shown in FIG. 13. Accordingly, after scanning of a patient, at least a portion 171 of positioning fixture 162 is removed from the skull 160, including attachment member 163 being secured in a fixed relationship with respect to the positioning fixture portion 171, as previously described. If it is then disposed within phantom fixture 172 as previously described, the means for orientating 202, or mating tongue and groove connection 203, will insure that the positioning fixture portion 171 is precisely and accurately orientated with respect to both the support surface 165 and the phantom fixture 172. Alternatively, the means for orientating 202 attachment member 163 with respect to both the support surface 165 and the phantom fixture 172 can comprise utilizing a single elongate rod without a mating tongue and groove connection 203, and using a means for orientating 202 comprised of a pin 206 which is engageable with a slotted support member 207 disposed on bracket 167 as shown in FIGS. 2 and 3. Likewise, phantom fixture 172 would be provided with the same type of slotted bracket 207 in lieu of lock member 191 (FIG. 13), whereby attachment member 163 will be accurately orientated with respect to both the support surface 165 and the phantom fixture 172.

Turning now to FIGS. 9–12, a positioning fixture 162 which comprises a portion of a system for performing stereotactic surgery, and which positioning fixture 162 may be utilized in connection with the method for performing stereotactic surgery previously described, will be set forth. Positioning fixture 162 which is adapted to be attached to skull 160 by at least one, and preferably two or more self-tapping screws 208, preferably comprises: a primary, or skull, plate member 209; guide plate member 210; cover plate member 211; secondary plate member 212; ball socket member 213; and attachment member 163. Primary, or skull plate member 209 is preferably an annular ring provided with at least one, and preferably two or more holes 214 through which screws 208 pass to engage skull 160. Skull plate member 209 is additionally provided with at least two alignment studs 215 which serve to accurately align guide plate member 210, cover plate member 211 and secondary plate member 212 with respect to the skull plate member 209, insofar as each of those components is provided with two openings 216 which mate with alignment studs 215 when those components are placed over skull plate member 209 and alignment studs 215. Guide plate member 210 is a generally annular member 217 having a downwardly depending annular flange member 218, and guide plate member overlies skull plate member 209 with the depending flange 218 being disposed within skull plate member 209. Cover plate member 211 is a flat disk which seals off the exposed portion of skull 160 lying beneath the opening defined by guide plate member 210 and skull plate member 209 when the secondary plate member 212 is not associated with skull plate member 209, as will be hereinafter described in greater detail. Of course, when it is desired to perform stereotactic surgery upon skull 160, in accordance with a method such as that previously described, cover plate member 211 would not be utilized in conjunction with positioning fixture 162.

Still with reference to FIGS. 9–12, secondary plate member 212 is a generally annular shaped member 219, which upon being passed over alignment studs 215 overlies skull plate member 209. Secondary plate member 212 may include a lower downwardly depending flange member 220 which closely conforms to the outer configuration of cover plate member 211 and guide plate member 210. Secondary plate member 212 is also provided with an interior annular opening 221 which has an inwardly extending annular flange member 222, within which opening 221 the ball socket member 213 may be received, and the downward movement of the ball socket member 213 is restrained by the internal annular flange member 222. Ball socket member 213 may preferably comprise an annular disk member 223 having an upwardly extending cup-like flange 224 which is adapted to receive the attachment member 163. Ball socket member 213 may be provided with a slightly bevelled internal surface 225 (FIGS. 9 and 12) upon which positioning ball 169 of attachment member 163 rests. As seen in FIG. 9, attachment member 163 may be an elongate rod 205 threadably received within positioning ball 169.

The upwardly extending cup-like flange 224 of ball socket member 213 may have one or more sections removed therefrom, as shown at 226, to permit greater flexibility of movement of attachment member 163, or rod 205, in that positioning ball 169 could be rotated until rod 205 is disposed within area 226. Secondary plate member 212 is preferably provided with a means for locking 228 the ball socket member 213 with respect to the secondary plate member 212. Preferably, the locking means 227 comprises at least one, and preferably two upstanding threaded posts 228 and mating lock nuts which are capable of bearing down upon the annular disk member 223 of ball socket member 213 as illustrated in FIG. 9. In this regard, secondary plate member 212 may be slightly spot-faced adjacent threaded posts 228, as shown at 230 to enable lock nuts 229 to contact annular disk member 223 of ball socket member 213, when ball socket member 213 is disposed within secondary plate member 212. As previously described, a means for locking 170 positioning ball 169 with respect to positioning fixture 162 may be provided, as by disposing at least one or more threaded screws 231 which pass through the upwardly extending cup-like flange 224 of ball socket member 213 to engage positioning ball 169. Mating lock nuts 232 may be provided for alignment studs 215, whereby, as shown in FIG. 9, secondary plate member 212, cover plate member 211, and guide plate member 210 may be firmly secured to skull 160, upon tightening of lock nuts 232. Lock nuts 232 will also serve to restrain outward movement of ball socket member 213 from positioning fixture 162; however, ball socket member 213 would be free to rotate within annular opening 221 unless lock nuts 229 were tightened to engage the upper surface of annular disk member 223 of ball socket member 213.

When utilizing the positioning fixture 162 as shown in FIGS. 9-12 to practice the method for performing stereotactic surgery previously described, positioning fixture 162 would initially be disposed as illustrated in FIG. 9 upon skull 160, with ball socket member 213 freely rotatable with respect to secondary plate member 212, and attachment member 163 would likewise be free to rotate with respect to ball socket member 213. Upon establishing the first, predetermined geometric relationship illustrated and described in connection with FIGS. 2 and 3, locking means 227 for ball socket member 213 would be secured, as well as engaging locking means 170 with positioning ball 169. After the scanning procedure has been conducted, as previously described, a portion of the positioning fixture 162 is then transferred to the phantom fixture 172 as previously described. When utilizing the positioning fixture of 162 as illustrated in FIGS. 9-12, lock nuts 232 are removed and the secondary plate member 212, with the ball socket member 213 firmly locked therein, and with positioning ball 169 firmly locked within ball socket member 213, is removed from the skull 160. Lock nuts 232 may then be threaded upon alignment studs 212 to secure the cover plate member 211 and guide plate member 210 to the skull plate member 212 which remains firmly affixed to the skull. Thus, as previously described in connection with FIG. 4, the secondary plate member 212, ball socket member 213 and attachment member 163, or positioning ball 169 and rod 205 may be disposed within the phantom fixture 172 in the manner previously described.

FIGS. 14 and 15 illustrate the positioning fixture 162 when a trajectory ball 194 has been substituted for the positioning ball 169, with the trajectory and distance of the medical instrument 197 to the target having been determined as previously described. In this regard, FIG. 14 illustrates the insertion of the medical instrument 197 through positioning fixture 162 via trajectory ball 194 and its passageway 196, until medical instrument 197 intersects target 161 disposed within skull 160. Of course, cover plate member 211 is not utilized in conjunction with positioning fixture 162 when medical instrument 197 is being inserted through positioning fixture 162.

The components of positioning fixture 162 may be made of any suitable material having the requisite strength characteristics and ability to maintain close tolerances upon exposure to a source of heat necessary to sterilize the components. Preferably, skull plate member 209, guide plate member 210, cover plate member 211, secondary plate member 212, ball socket member 213, positioning ball 169 and trajectory ball 194 are all manufactured of LEXAN ®.

With reference to FIG. 13, additional features of a phantom fixture 172, which forms a part of the system for performing stereotactic surgery, and is useful in the practicing of the method for performing stereotactic surgery previously described, are shown. Phantom fixture 172 preferably includes two pair of guide rods 233, 234, disposed perpendicular to each other. Guide rods 234 are slideably mounted upon guide rods 233, as by mounting blocks 235. At least one guide block 235 is provided with a locking means 236 which permits the fixing of the x-coordinate for phantom target rod 237. Phantom target rod 237 is associated with a slideable mounting block 238 which is slideable along guide rod 234. Mounting block 238 has a locking means 239 which permits locking the phantom target rod 237 in the desired y-coordinate. Phantom target rod 237 is in turn vertically slideable within mounting block 238 whereby the z-coordinate of phantom target 174 can be established by engaging a locking means 240 which engages phantom target rod 237.

Figure 7:
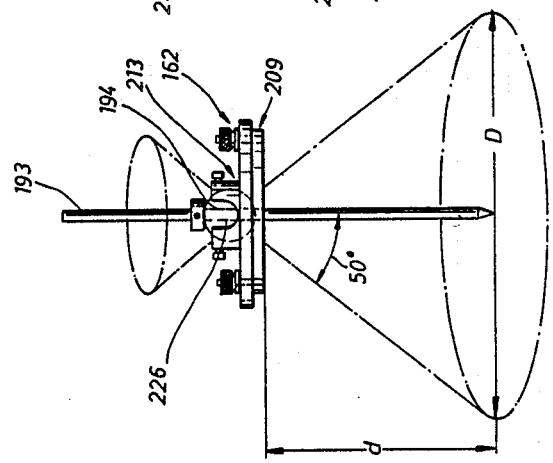
FIG. 7 is a front view of a positioning fixture in accordance with the present invention, illustrating the intracranial area accessibility of a positioning fixture of the present invention.

With reference to FIG. 7, a positioning fixture 162 in accordance with the present invention is shown having a medical instrument 193 inserted therethrough via a trajectory ball 194 disposed within ball socket member 213 and skull plate member 209. Due to the rotatability of the ball socket member 213 with respect to the skull plate member 209, as well as the open areas 226 formed in ball socket member 213, positioning fixture 162 allows full access to a diameter (D) slice of brain at a depth (d), wherein the diameter can be as large as 14 cm. and the depth can be up to 6 cm. Thus, multiple targets within the skull 160 can be intersected by medical instrument 193 from a single attachment of positioning fixture 162 to skull 160. Additionally, it should be noted that trajectory balls 194 could be utilized having multiple parallel passageways 196 disposed therein, whereby more than one medical instrument can intersect a potential target within the skull 160.

With reference to FIG. 8, an accessory stanchion clamp 250 is illustrated. Stanchion clamp 250 has at its lower end, a bracket 251 which is adapted to engage the secondary plate member 212 which has been affixed to the skull (not shown) as previously described. Bracket 251 may include a locking means 252, or threaded locking screw 253 which engages the upper surface of secondary plate member 212. The stanchion clamp 250 may further include a slot 254 through which a medical instrument 193 may pass, and a medical instrument locking means 255 or threaded locking screw 256, is provided to lock the medical instrument 193 with respect to the stanchion clamp 250. Stanchion clamp 250 can be utilized to perform stereotactically guided craniotomies through an opening as large as 3 cm. in diameter, as well as allows for the use of endoscopes, lasers, and ultrasound devices within the skull. After the trajectory and distance of medical instrument 193 to the target have been determined in the manner previously described, the positioning fixture portion 171 with trajectory ball 194 therein is secured to skull plate member 209. Stanchion clamp member 250 is then attached to the secondary plate member 212, whereby medical instrument 193 may pass through the trajectory ball (not shown). Upon removal of the ball socket member 213, including the trajectory ball 194, positioning fixture 162 with stanchion clamp 250 would appear as illustrated in FIG. 8, whereby greater access is allowed to the interior of the skull. Additionally, stanchion clamp 250 supports lineal movement of the medical instrument 193 along the x and y axes, and can thus provide parallel access to intracranial lesions without the necessity of redetermining trajectories. Alternatively, bracket 251 could be a two part, hinged ring which snaps onto and around secondary plate member 212.

With reference now to FIGS. 16–23, an apparatus 250 (FIG. 22) useful for performing stereotactic surgery will be described. Many of the components of apparatus 250 are identical to those previously described in connection with the embodiments of FIGS. 1–15 previously described, and the same reference numerals are utilized in FIGS. 16–23. Components similar in construction to those previously described will bear primed reference numerals. The apparatus 250 of FIGS. 16–23 permits a medical instrument 193 to intersect the target 161 within skull 160 by entering the skull 160 from a choice of a plurality of locations upon the skull 160, rather than only enter the skull from a single location as illustrated in FIG. 6. The advantages of being able to enter the skull 160 from a choice of a plurality of different locations upon the skull 160 are numerous. The skull plate member 209 of the positioning fixture 162 can be applied at any convenient site upon the skull 160, rather than over the target 161, as illustrated in FIG. 6. For posterior fossa, transphenoidal, and temporal fossa targets, such placement is especially advantageous. Biopsying through a previously placed burr hole or craniotomy is much more straight forward, when the ability exists to place the skull plate member 209 of positioning fixture 162 at any convenient location upon skull 160. As will be hereinafter described in greater detail, the performing of stereotactic craniotomies, interstitial implants indepth electrode placements and recordings becomes a more routine process.

Figure 17:
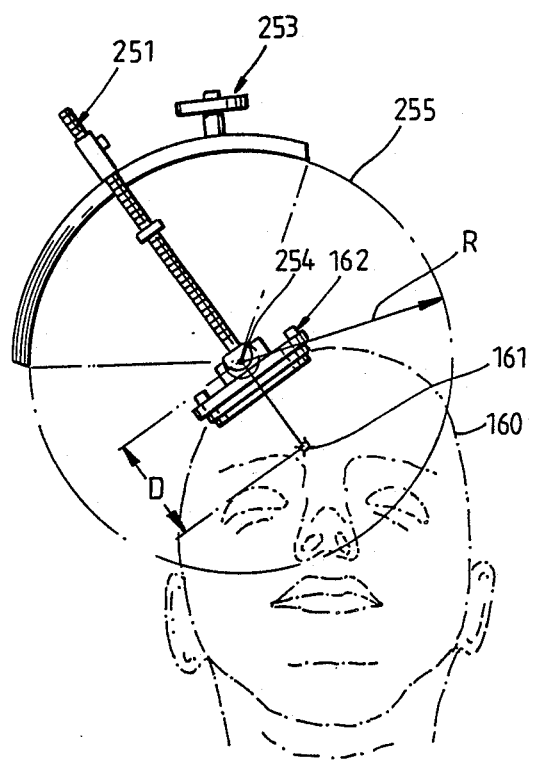

With reference now to FIGS. 16–19, and FIG. 22, the principles of operation of the apparatus 250 of the present invention will be described. A positioning fixture 162, as will be hereinafter described in greater detail in connection with FIGS. 20–21, is illustrated to generally include a carrier member 251 associated with positioning member 162, an arc member 252 associated with the carrier member 251, and an instrument guide member 253 associated with the arc member 252. Arc member 252 has a pre-determined radius of curvature R, whereby all radii, having radius of curvature R, extending from the arc member 252 will intersect at a common point, such as point 254 in FIG. 16, which is the center of an imaginary sphere 255. Thus, a medical instrument 193, if caused to pass through instrument guide member 253 disposed anywhere on arc member 252 would intersect with point 254. It should be understood that were the arc member 252 to be associated with carrier member 251 at a lower position upon carrier member 251 from that shown in FIG. 16, the point of intersection of 254 of the radii having a radius of curvature R would likewise be moved lower. FIG. 17 illustrates positioning fixture 162 disposed upon a patient's skull 160 in a location similar to that shown and previously described in connection with FIG. 6. Arc member 252 and its associated instrument guide member 253 are disposed upon carrier member 251 in the same position illustrated in FIG. 16, whereby the point of intersection of all radii of arc member 252, having a pre-determined radius of curvature R, would intersect at point 254.

Figure 18:
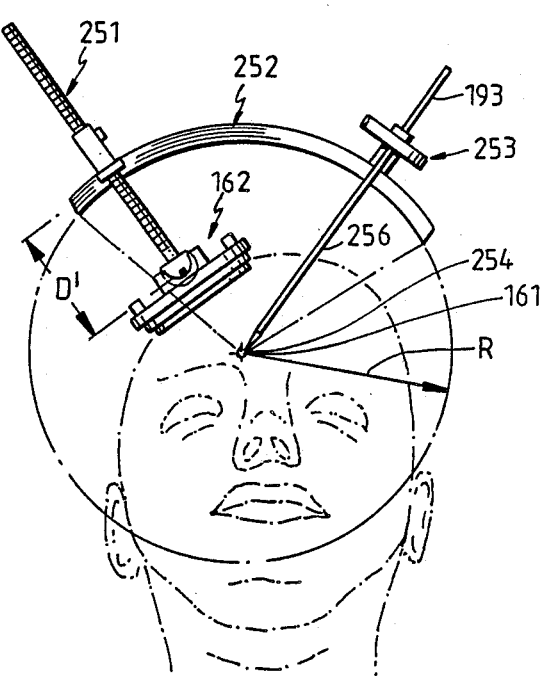

FIG. 18 illustrates arc member 252 and its associated instrument guide member 253 having been moved downwardly along carrier member 251 a distance equal to the distance D between point 254 and the target 161 of FIG. 17. With the carrier member 251 and arc member 252 disposed in the position illustrated in FIG. 18, all radii extending from arc member 252, and having the predetermined radius of curvature R, will intersect at point 254 which coincides with the target 161. Thus, instrument guide member 253 can be moved anywhere along arc member 252 and medical instrument 193, upon being inserted a distance equal to the radius of curvature R, will intersect target 161 within skull 160. Furthermore, it should be noted that since intersection point 254 (FIG. 16) corresponds to the center of an imaginary sphere 255, rotation of arc member 252 about carrier member 251, will still result in all of the radii, having a radius of curvature R, from arc member 252 intersecting point 254, which coincides with target 161 (FIG. 18). Thus, with reference to FIGS. 18 and 19, the entry point, or burr hole, 256 formed in skull 160 can be disposed on virtually any part of skull 160, because the trajectory of medical instrument 193 can be adjusted by not only moving instrument guide member 253 along arc member 252, but also by rotating arc member 252 about carrier member 251 to permit medical instrument 193 to enter the skull 160 at any of a plurality of locations 256 upon skull 160 in order to intersect target 161 within skull 160.

In order to use apparatus 250 in the manner previously described in connection with FIGS. 16–19, the trajectory and distance of a medical instrument 193 extending from the positioning fixture portion 171 to the phantom target 174 is determined in the same manner as that previously described in connection with FIGS. 1–15 with the following exception. Instead of utilizing a trajectory ball 194 in connection with the positioning fixture portion 171 in phantom fixture 172, an arc-trajectory ball 194' (FIGS. 20–21) is utilized as will be hereinafter described in greater detail. Arc-trajectory ball 194' differs from trajectory ball 194 in that arc-trajectory ball 194' preferably includes a passageway 196' disposed within arc-trajectory ball 194' extending through a portion thereof, and is adapted to permit the medical instrument 193 to pass through the arc-trajectory ball 194'. Arc-trajectory ball 194' also includes means for attaching 257 carrier member 251 to arc-trajectory ball 194'. Preferably, attachment means 257 comprises a mating threaded connection 258 between carrier member 251 and arc-trajectory ball 194'.

Thus, the trajectory and distance of the medical instrument extending from the positioning fixture portion 171 to the phantom target 174 is then determined by inserting a medical instrument 193 through the positioning fixture portion 171 until it intersects the phantom target 174 as illustrated in FIG. 5. Medical instrument 193 may then be locked with respect to the positioning fixture portion 171 at the desired trajectory and distance to the phantom target 174. This step may be accomplished by: associating an arc-trajectory ball 194' with the positioning fixture portion 171; inserting the medical instrument 193 through the arc-trajectory ball 194'; and adjusting it until it intersects the phantom target 174 as shown in FIG. 5. Arc-trajectory ball 194' may then be locked with respect to positioning fixture portion 171, as by engaging positioning ball locking means 170 with arc-trajectory ball 194'. For example, positioning ball locking means 170, which can also be used to lock arc-trajectory ball 194', is preferably at least one, or more, locking screws 231 that securely engage arc-trajectory ball 194' and fix its position with respect to positioning portion 171.

After arc-trajectory ball 194' has been locked with respect to positioning fixture portion 171, whereby medical instrument 193 has intersected phantom target 174, the distance from the positioning fixture portion 171 to the phantom target 174 is preferably indicated. The indication of this distance can be accomplished by either associating the depth stop member 197 with the medical instrument 193 (FIG. 5) after arc-trajectory ball 194' has been locked with respect to positioning fixture 171; or the distance may be directly measured in a conventional manner.

Upon completion of the step of determining the trajectory and distance of the medical instrument 193 to the phantom target 174, positioning fixture portion 171 having arc-trajectory ball 194' locked therein is attached to the skull 160 in the same location that it was originally attached to the skull 160 as previously described in connection with FIG. 6. Carrier member 251, arc member 252 and instrument guide member 253 are then attached to positioning fixture 162, as by threading carrier member 251 into the arc-trajectory ball 194'. The distance D between the target 161 and positioning fixture 162, which has been determined in the manner previously described, is then subtracted from the pre-determined radius R of arc member 252. Arc member 252 is then disposed upon carrier member 251 at a distance D' (FIG. 18) from positioning fixture 162, which distance D' is equal to the pre-determined radius of curvature R less the distance D'. A suitable depth stop member 197 as previously described in connection with FIG. 14 may be utilized to fix the location of arc member 252 with respect to carrier member 251. Thereafter, instrument guide member 253 and arc member 252 are adjusted to obtain the desired entry point 256 into skull 160, whereby medical instrument 193 is inserted through the instrument guide member 253 to intersect target 161. The medical instrument 193 is inserted a distance equal to the pre-determined radius of curvature R of arc member 252.

With reference now to FIGS. 20-23, the apparatus 250 of the present invention will be described in greater detail. Apparatus 250 includes a positioning fixture 162 which includes: a skull plate member 209, guide plate member 210; secondary plate member 212, ball socket member 213; means for aligning the skull plate member 209 and secondary plate member 212, or alignment studs 215 and lock nuts 232; and means for locking 228' the ball socket member 213 with respect to the secondary plate member 212. All of the foregoing components with the exception of the locking means 228' are identical to those components previously described in connection with FIGS. 14-15. Locking means 228' has been modified to the extent that an annular plate member 260 overlies ball socket member 213 and is rotatably mounted upon annular disk member 223 by a lock ring 261, whereby ball socket member 213 can rotate with respect to annular plate member 260. Annular plate member 260 includes a key receiving opening 262 which mates with a moveable key 263 disposed upon secondary plate member 212 which key 263 may be secured via a locking screw 264. A hold down screw 265 is disposed opposite key 263 upon secondary plate member 212, whereby ball socket member 213 and annular plate member 260 are received within secondary plate member 212 by insertion of key 263 into key receiving opening 262. Accordingly, ball socket member 213 is rotatably received within secondary plate member 212. Ball socket member 213 may then be locked with respect to secondary plate member by tightening down two locking bolts 266 within two threaded openings 267 formed in the annular plate member 260, whereby the two locking bolts 266 bear down upon annular disk member 223 of ball socket member 213 to fixedly secure ball socket member 213 with respect to secondary plate member 212.

Still with reference to FIGS. 20-23, an arc-trajectory ball 194' as previously described, is disposed within ball socket member 213 and may be fixedly secured within ball socket member 213 as by locking means 170. Carrier member 251 is preferably attached to the arc-trajectory ball 194' as by connection means 257, or mating threaded connection 258, as previously described. Arc-carrier 251 is preferably an elongate rod member having a plurality of equidistant distance indicia 269' appearing thereon. It should of course be readily apparent to one of ordinary skill in the art that the cross-sectional configuration of carrier member 251 could be any suitable configuration, as well as any suitable connection means 257 could be utilized. Arc member 252 could be attached directly to carrier member 251; however, it is preferable that arc member 252 be attached to carrier member 251 via an adjustable arc member carrier block 270. Arc member carrier block 270 preferably includes means for releaseably and adjustably locking 271 arc member carrier block 270 to carrier member 251, which locking means 271 may preferably be a locking screw 272 which engages the elongate rod 269 of carrier member 251. Arc member carrier block 270 may also preferably include means for releaseably and adjustably securing 273 arc member 252 to arc member carrier block 270, such as a locking bolt 274. Arc member 252 may be further releaseably and adjustably secured to the arc member carrier block member 270 as by a tongue and grove connection 275, wherein a grove 276 is formed in the outer surface of arc member 252, which grove 276 cooperates with a tongue or key disposed upon arc member carrier block 270. It should be understood that any suitable means for releaseably and adjustably securing 273 arc member 252 to arc member carrier block 270 may be utilized. Preferably, are member 252 may be moveable with respect to arc member carrier block 270 in the direction shown by arrows 276 in FIG. 22. Furthermore, arc member carrier block 270 is preferably rotatable about carrier member 251, as previously described in connection with FIGS. 16–19.

Instrument guide member 253 is also mounted on the arc member 252. Preferably, instrument guide member 253 is releaseably and adjustably secured to arc member 252 as by a instrument guide member carrier block 278 which is similar in construction to arc member carrier block 270, and also includes a locking bolt 274. Instrument guide member carrier block 278 may also preferably be moveably mounted upon arc member 252 as by a similar tongue and grove connection previously described in connection with arc member carrier block 270, and is also moveable in the direction shown by arrows 277 in FIG. 22.

Figure 23:
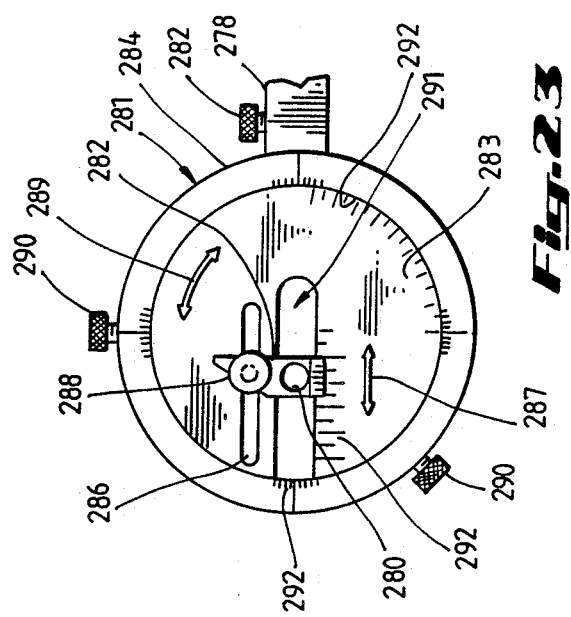
FIG. 23 is a top view of the instrument guide member of FIG. 22.
Figure 22:
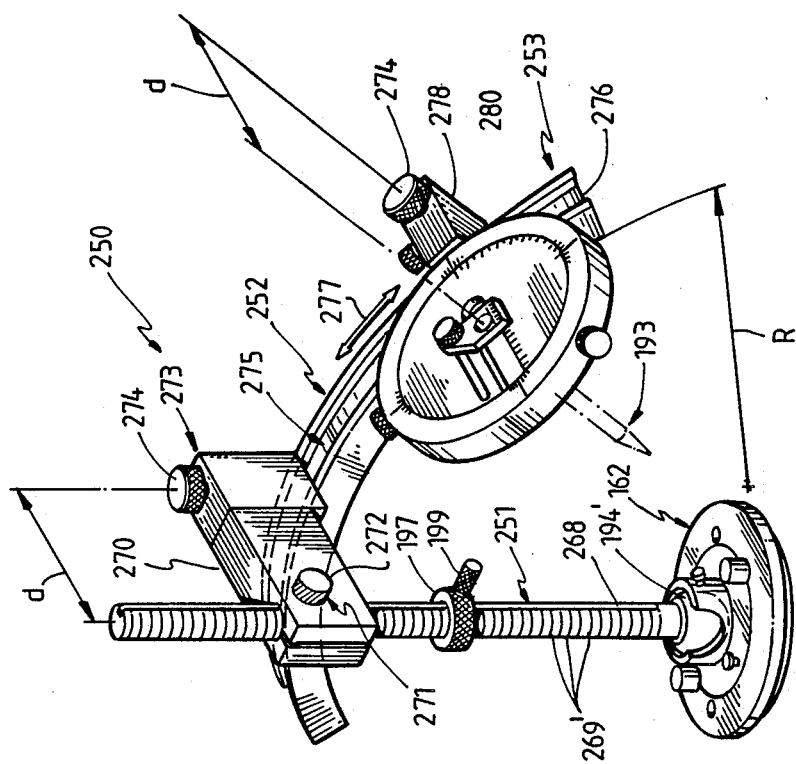
FIG. 22 is a plane view of the apparatus of FIG. 20, including an arc member and an instrument guide member.

With reference now to FIGS. 22 and 23, the instrument guide member 253 will be described in greater detail. Preferably instrument guide member 253 has an opening 280 formed therein for guiding medical instrument 193 as the medical instrument 193 passes downwardly through opening 280 to intersect the desired target within the skull. Instrument guide member 253 could comprise a tubular member (not shown) having opening 280 formed therein and the tubular member could be disposed upon instrument guide member carrier block 278. In this regard, it should be noted that in order for medical instrument 193 to intersect the desired target within skull 160, the longitudinal axis of opening 280 and carrier member 251 must lie in a place which is parallel with a plane formed by the longitudinal axis of the arc member 252. Since the center line, or longitudinal axis, of arc member 252 is offset from carrier member 251 by a distance d, as a result of the inclusion of arc member carrier block 270, the center line distance between opening 280 and arc member 252 caused by instrument guide member carrier block 278 must be the same distance d, as shown in FIG. 22.

Preferably instrument guide member 253 includes means for moving 281 opening 280 with respect to the instrument guide member 253. Moving means 281 is preferably provided by forming opening 280 within a moveable block 282 and block 282 is moveably disposed within a rotatable disk member 283, which disk member 283 is rotatably received within an outer ring member 284. Outer ring member 284 is releaseably secured to instrument guide member carrier block 278, as by a key member (not shown) which is received within the instrument guide member carrier block 278 and secured by a locking screw 285. Moveable block 282, having opening 280 therein, is journaled for movement along a slot 286 formed in rotatable disk member 283 for movement in the direction of arrows 287. The location of moveable block 282 can be fixed via a locking screw 288. Rotatable disk member 283 may rotate in the direction shown by arrows 289 which movement may be restrained by locking screws 290. The center of opening 280 in FIG. 22 corresponds to a zero setting (shown at 291 in FIG. 23) wherein medical instrument 193 will intersect with the target 161 within skull 160. In FIG. 23, the opening 280 has been moved with respect to the instrument guide member 253, via movement of moveable block 282, whereby a medical instrument may be guided to a position slightly offset from target 161 within skull 160. Rotatable disk member 283 and outer ring member 284 are provided with suitable indicia 292, whereby the amount of offset of opening 280, both longitudinal and angular displacement, may be determined. The ability to guide a medical instrument 193 to pre-determined locations within the skull 160 which locations are offset from the target 161 within skull 160 is particularly useful in certain medical procedures.

All of the foregoing components of apparatus 250 are formed of a material having the requisite strength and rigidity characteristics, as well as being capable of being sterilized for use in an operating room environment. In this regard, the components of apparatus 250 may be manufactured of materials such as stainless steel, aluminum, and various plastic materials, as would be readily apparent to one of ordinary skill in the art.

It is to be understood that the invention is not limited to the exact details of construction, operation, exact materials, or embodiment shown and described as obvious modifications and equivalents will be apparent to one skilled in the art; for example, more than one instrument guide member could be disposed upon the arc member. Accordingly, the invention is therefore to be limited only by the scope of the appended claims.

I claim:

1. A method for performing stereotactic surgery with a medical instrument upon a target within a skull, comprising the steps of:
    (a) establishing a first, predetermined geometric relationship between a positioning fixture attached to both the skull and to a support surface upon which the skull is disposed;
    (b) scanning the skull to produce an image of the target within the skull with respect to the positioning fixture;
    (c) transferring at least a portion of the positioning fixture to a phantom fixture and disposing the portion of the positioning fixture from the positioning fixture with respect to the phantom fixture to establish a second, predetermined geometric relationship therebetween, which is identical to the first, predetermined geometric relationship, whereby the slope of the skull where the positioning fixture is attached to the skull is duplicated within the phantom fixture;
    (d) disposing a phantom target within the phantom fixture at a location which corresponds to the location of the target within the skull;
    (e) determining the trajectory and distance of a medical instrument extending from the positioning fixture portion to the phantom target;
    (f) attaching the portion of the positioning fixture upon the skull in the same location it was originally attached to the skull;
    (g) attaching a carrier member, arc member, and instrument guide member to the positioning fixture; and
    (h) inserting the medical instrument through the instrument guide member, whereby the medical instrument will intersect the target in the skull.

2. The method of claim 1, wherein the positioning fixture is attached to the support surface by an attachment member having first and second end portions, and the first, predetermined geometric relationship is the attachment member disposed coplanar with the support surface; and the second, predetermined geometric relationship is the attachment member disposed coplanar with the phantom fixture.

3. The method of claim 2, including the steps of: moveably associating the first end portion of the attachment member with respect to the positioning fixture; and securing the attachment member with respect to the positioning fixture prior to scanning the skull.

4. The method of claim 3, including the steps of: moveably associating the attachment member with respect to a portion of the positioning fixture by using a positioning ball secured to the first end portion of the attachment member; and the positioning ball is rotatably received within the positioning fixture.

5. The method of claim 4, including the steps of using as the attachment member an elongate rod, which includes a means for identically orientating the second end portion of the attachment member with respect to both the support surface and the phantom fixture.

6. The method of claim 5, including the steps of: using a mating tongue and groove connection as the means for identically orientating the second end portion of the attachment member; and associating the mating tongue and groove connection with the second end of the attachment member and an end of an elongate rod disposed coplanar with the support surface and the phantom fixture.

7. The method of claim 1, including the steps of: using an outer and inner gimbal in the phantom fixture; and disposing the positioning fixture portion within the inner gimbal in the second geometric relationship.

8. The method of claim 7, wherein the positioning fixture is attached to the support surface by an attachment member having first and second end portions; the first, predetermined geometric relationship is the attachment member disposed coplanar with the support surface; the second geometric relationship is the attachment member disposed coplanar with the phantom fixture; and, while the positioning fixture portion is fixed with respect to the attachment member, the outer and inner gimbals are adjusted to receive the positioning fixture portion.

9. The method of claim 8, including the steps of locking the inner and outer gimbal with respect to the phantom fixture; securing the positioning fixture portion within the inner gimbal; and determining the trajectory and distance of the medical instrument by: inserting the medical instrument through the positioning fixture until it intersects the phantom target; and locking the medical instrument with respect to the positioning fixture at the desired trajectory and distance.

10. The method of claim 9, wherein the medical instrument is locked with respect to the positioning fixture portion by: associating an arc-trajectory ball with the positioning fixture portion; inserting the medical instrument through the arc-trajectory ball until it intersects the phantom target; and locking the arc-trajectory ball with respect to the positioning fixture portion.

11. The method of claim 10, including the step of indicating the distance from the positioning fixture to the phantom target when the medical instrument has intersected the phantom target.

12. The method of claim 11, wherein the distance is indicated by associating a depth stop member with the medical instrument after the arc-trajectory ball has been locked.

13. The method of claim 11, including the step of removing the medical instrument from the arc-trajectory ball, and the carrier member is attached to the positioning fixture by attaching the carrier member to the locked arc-trajectory ball.

14. The method of claim 1, including the step of locating the instrument guide member upon the arc member, whereby the medical instrument may enter the skull at a desired location upon the skull.

15. The method of claim 14, further including the step of rotating the arc member about the carrier member, whereby the medical instrument may enter the skull at a desired location upon the skull.

16. A system for performing stereotactic surgery with a medical instrument upon a target within a skull, comprising:
 (a) a positioning fixture, having associated therewith, a means for attaching the positioning fixture to both the skull and to a support surface upon which the skull is disposed; the positioning fixture including means for establishing a first, predetermined geometric relationship between the positioning fixture and the support surface;
 (b) a phantom fixture, including: means for receiving at least a portion of the positioning fixture; means for establishing a second predetermined geometric relationship between the positioning fixture portion and the phantom fixture, wherein the second geometric relationship is identical to the first geometric relationship, whereby the slope of the skull where the positioning fixture is attached to the skull may be duplicated within the phantom fixture;
 (d) the means for attaching the positioning fixture including an attachment member having first and second end portions; in the first, predetermined geometric relationship, the attachment member is disposed coplanar with the support surface; and in the second, predetermined geometric relationship, the attachment member is disposed coplanar with the phantom fixture; and
 (d) a carrier member adapted for attachment to the positioning fixture, an arc member, adapted for attachment to the carrier member, and an instrument guide member, adapted to be attached to the arc member, whereby the medical instrument may be passed through the instrument guide member to intersect the target by entering the skull at a plurality of locations upon the skull.

17. The system of claim 16, wherein the means for establishing the first, predetermined geometric relationship, includes the first end portion of the attachment member being moveably associated with respect to the positioning fixture; and the positioning fixture includes means for locking the attachment member with respect to at least a portion of the positioning fixture.

18. The system of claim 17, wherein the first end portion of the attachment member has a positioning ball associated therewith; and a portion of the positioning fixture includes means for rotatably receiving the positioning ball therein.

19. The system of claim 18, wherein the rotatable receiving means comprise a ball socket member which permits the first positioning ball to rotate therein; the ball socket member being rotatably mounted with respect to at least a portion of the positioning fixture and includes means for locking the ball socket member with respect to at least a portion of the positioning fixture.

20. The system of claim 19, wherein the ball socket member has an arc-trajectory ball disposed therein, upon the removal of the positioning ball.

21. The system of claim 20, wherein the arc-trajectory ball has a passageway therethrough adapted to permit a medical instrument to pass through the arc-trajectory ball.

22. The system of claim 21, wherein the arc-trajectory ball includes means for attaching the carries member to the positioning fixture.

23. The system of claim 16, wherein the instrument guide member includes means for guiding the medical instrument to predetermined locations within the skull which locations are offset from the target in the skull.

24. An apparatus, useful for performing stereotactic surgery, comprising:
   (a) a skull plate member, adapted to be secured to a skull;
   (b) a secondary plate member, adapted to overlie the skull plate member;
   (c) a ball socket member rotatably received within the secondary plate member;
   (d) means for aligning the skull plate member and secondary plate member with respect to one another;
   (e) means for locking the ball socket member with respect to the secondary plate member;
   (f) an arc-trajectory ball disposed within the ball socket member;
   (g) a carrier member attached to the arc-trajectory ball;
   (h) an arc member mounted on the carrier member, the arc member being curved substantially along the entire length of the arc member and having a predetermined radius of curvature; and
   (i) means for guiding an instrument away from the arc-trajectory ball, the guiding means being mounted on the arc member, and moveable along the arc member.

25. The apparatus of claim 24, including means for locking the arc-trajectory ball within the ball socket member.

26. The apparatus of claim 24, wherein the arc member is adjustably mounted on the carrier member.

27. The apparatus of claim 24, wherein the instrument guide member is adjustably mounted on the arc member.

28. The apparatus of claim 24, wherein the instrument

* * * * *

UNITED STATES PATENT AND TRADEMARK OFFICE
CERTIFICATE OF CORRECTION

PATENT NO. : 4,955,891
DATED : September 11, 1990
INVENTOR(S) : Mark P. Carol

It is certified that error appears in the above-identified patent and that said Letters Patent is hereby corrected as shown below:

In Claim 28, after "instrument", insert --guide member includes an opening for guiding a medical instrument and means for moving the opening with respect to the instrument guide member--.

Title page: Item (63) under Related U.S. Application Data, delete "4,805,815", and insert --4,805,615--.

Signed and Sealed this

Fourth Day of February, 1992

Attest:

HARRY F. MANBECK, JR.

Attesting Officer

Commissioner of Patents and Trademarks